United States Patent [19]

Colbry

[11] 4,376,858

[45] Mar. 15, 1983

[54] 2-4-DIAMINO-5-METHYL-6-[(3,4,5-TRIME-THOXYANILINO)METHYL]QUINAZOLINE SALTS

[75] Inventor: Norman L. Colbry, Gregory, Mich.

[73] Assignee: Warner Lambert Company, Morris Plains, N.J.

[21] Appl. No.: 344,350

[22] Filed: Jan. 29, 1982

Related U.S. Application Data

[63] Continuation of Ser. No. 202,512, Oct. 31, 1980, abandoned.

[51] Int. Cl.³ ................. C07D 239/84; A61K 31/505
[52] U.S. Cl. ..................................... 544/291; 424/251
[58] Field of Search ........................ 544/291; 424/251

[56] References Cited

U.S. PATENT DOCUMENTS

| | | | |
|---|---|---|---|
| 3,471,498 | 10/1969 | Davoll | 544/291 |
| 3,485,842 | 12/1969 | Davoll | 544/291 |
| 3,560,502 | 2/1971 | Davoll | 544/291 |

FOREIGN PATENT DOCUMENTS

| | | | |
|---|---|---|---|
| 1104576 | 2/1968 | United Kingdom | 544/291 |
| 1345502 | 1/1974 | United Kingdom | 544/291 |

OTHER PUBLICATIONS

McElvain, *The Characterization of Organic Compounds*, Revised Edition, 1953, The Macmillian Co., pp. 44–47; 72–75.

Berge, et al., "J. Pharm. Sci.," vol. 66, No. 1, 1977, pp. 1–19.

*Primary Examiner*—Donald G. Daus
*Assistant Examiner*—James H. Turnipseed
*Attorney, Agent, or Firm*—Ronald A. Daignault

[57] ABSTRACT

2,4-Diamino-5-methyl-6-[(3,4,5-trimethoxyanilino)methyl]quinazoline salts, pharmaceutical compositions containing said salts, methods of treating malaria, and bacterial infections employing said salts and compositions and methods for producing said salts.

5 Claims, No Drawings

2-4-DIAMINO-5-METHYL-6-[(3,4,5-TRIMETHOXYANILINO)METHYL]QUINAZOLINE SALTS

This is a continuation of application Ser. No. 202,512, filed Oct. 31, 1980 and now abandoned.

The compound 2,4-diamino-5-methyl-6-[(3,4,5-trimethoxyanilino)methyl]quinazoline is reported in Great Britain Patent Specification No. 1,345,502, which is incorporated by reference, as exhibiting antimalarial and antibacterial activity. This compound, which has the formula

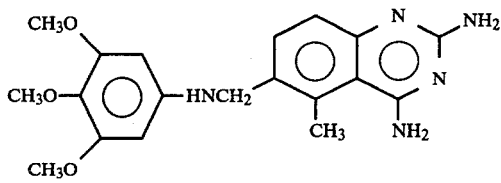

has also been reported to exhibit antineoplastic activity in Biochemical Pharmacology 28, 1983–1987(1978) and Cancer Research 39, 293–304(1979). Unfortunately, the salts that have been studied to date do not have a high degree of water solubility. This is especially deleterious when treating neoplasms since injectable routes are preferred.

Salts can be found to be unacceptable for a host of reasons: Lack of solubility, high toxicity, unstability, non-crystalline structure, not recognized as safe by the United States Food and Drug Administration, etc.

The present invention relates to soluble, nontoxic, stable, crystalline salts having the names 2,4-diamino-5-methyl-6-[(3,4,5-trimethoxyanilino)methyl]quinazoline monoisethionate and 2,4-diamino-5-methyl-6-[(3,4,5-trimethoxyanilino)methyl]quinazoline glucuronate.

The salts of the invention are shown by the following formula

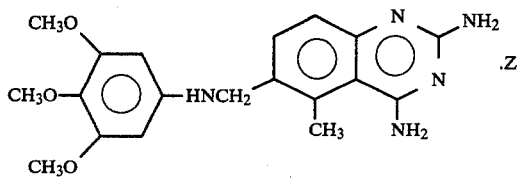

wherein Z is 2-hydroxyethanesulfonic acid or glucuronic acid. The term glucuronic acid is intended to encompass all the isomeric forms of glucuronic acid with the preferred form being the naturally occurring form of glucuronic acid.

The compounds of formula I wherein Z is 2-hydroxyethanesulfonic acid or glucuronic acid are prepared by reacting 2,4-diamino-5-methyl-6-[(3,4,5-trimethoxyanilino)methyl]quinazoline with 2-hydroxyethanesulfonic acid or glucuronic acid, respectively.

The ratio of reactants is not critical and while equimolar quantities of reactants may be employed an excess of acid is generally preferred.

The reaction is carried out in a polar solvent, such as methanol, ethanol, acetone, water, etc., or mixtures thereof. The reaction may be carried out at temperatures from about 0° C. to about 100° C. (depending on the boiling point of the solvents used) for periods of from about a few minutes to about twenty-four hours. A more preferred range of conditions is about 25° C. to about 80° C. for about one to eight hours.

It should be noted that the reaction can take place using a suspension of the base in the polar solvent.

The two compounds of the invention exhibit excellent properties for use as pharmaceuticals. The 2,4-diamino-5-methyl-6-[(3,4,5-trimethoxyanilino)methyl]quinazoline monoisethionate salt is a stable, crystalline, highly water soluble salt. The 2,4-diamino-5-methyl-6-[(3,4,5-trimethoxyanilino)methyl]quinazoline glucuronate salt appears to be powdery rather than crystalline, but has a higher degree of solubility.

These conclusions are based on the results of experiments reported in Tables I and II. Table I reports the results of experiments where 2,4-diamino-5-methyl-6-[(3,4,5-trimethoxyanilino)methyl]quinazoline is added to an aqueous acidic solution, while Table II reports the solubility of prepared 2,4-diamino-5-methyl-6-[(3,4,5-trimethoxyanilino)methyl]quinazoline salts. A comparison of the results obtained from the two methods is reported in Table III.

Most salts were found to have an unsatisfactory degree of solubility in water, such as the 2-naphthalene sulfonate; undesirable amorphous form, such as the gluconate or galacturonate, or not acceptable because extensive studies to determine safety would have to be performed, such as ethoxyacetic acid.

The compounds of this invention are useful in treating malaria or as an antibacterial in mammals, such as dogs, cats, cattle, etc., in dosage unit form with the dose adjusted to the needs and tolerances of the subject being treated. The usual mammalian dosage range for a 70 kg subject is from about 3.5 to 350 mg per day (0.05 mg to 5.0 mg per kg of body weight per day), preferably 7.0 mg to 140 mg per day (0.1 mg to 2.0 mg per kg of body weight per day).

TABLE I 2,4-Diamino-5-methyl-6-[3,4,5-trimethoxyanilino)-methyl]quinazoline Solubility in Aqueous Acids

| Acid | ph. 1 M soln. | Base Solubility in acid soln. |
|---|---|---|
| Glucuronic | 2.05 | 34.35 mg base/ml |
| Gluconic | 2.27* | 19.8 |
| Ethoxyacetic | 2.20 | 19.5 |
| Galacturonic | 2.28 | 25.1 |
| Ethoxyacetic | 2.35* | 19.7 |
| Isethionic | 1.20 | 16.3 |
| Isethionic | 1.46* | 17.3 |
| N—(Morpholine)ethane-2-sulfonic | 1.52 | 11.2 |
| Methane sulfonic | 1.00 | 9.83 |
| Methane sulfonic | 1.42* | 6.49 |
| Citric | 1.95 | 8.28 |
| Benzene sulfonic | 0.95 | 7.17 |
| Benzene sulfonic | 1.48* | 1.89 |
| Glycolic | 3.00 | 4.13 |
| Glycolic | 3.28* | 4.73 |
| p-Toluene sulfonic | 1.45 | 2.74 |
| d-Tartaric | 1.82 | 1.57 |
| (2-Pyridyl)-2-ethane sulfonic | 3.35 | 1.73 |
| 2-Amino-ethane sulfonic | 4.28 | .51 |
| 2-Naphthalene sulfonic | 1.05 | .15 max. |

*ph of .05 M acid - test method using 1/1 acid/base

Method: 0.1 M acid solutions, 10.0 ml, prepared—185±3 mg of 2,4-diamino-5-methyl-6-[(3,4,5-trimethoxyanilino)methyl]quinazoline added (0.05 M in base)—the mixture shaken 4–12 hours, filtered, and 1.0 ml of filtrate diluted with 0.01 NHCl to read UV absorbance at 321 nm.

TABLE II

Solubility of 2,4-Diamino-5-methyl-6-[(3,4,5-trimethoxyanilino)methyl]quinazoline Salts in Water

| Salt | Method | Solubility mg base/ml |
|---|---|---|
| Glucuronate | B | 109.4 |
| Isethionate | B | 24.78 |
| Isethionate | A | 23.93 |
| Ethoxyacetate | B | 6.3 |
| 3-Hydroxypropyl sulfonate | B | 4.73 |
| Lactate | A | 4.34 |
| Hydrochloride | A | 3.22 |
| Gluconatete | B | 2.55 |
| Ethane sulfonate | B | 2.64 |
| Acetate | A | 1.72 |
| Sulfate | A | 1.61 |
| Gentisate | A | 1.4–7.06* |
| Gentisate | B | 0.28 |
| Benzene sulfonate | B | 1.24 |
| Free base - 2,4-diamino-5-methyl-6-[(3,4,5-trimethoxyanilino)methyl]quinazoline | A | 0.2 |
| Free base - 2,4-diamino-5-methyl-6-[(3,4,5-trimethoxyanilino)methyl]quinazoline | B | 0.1 |

*Analytical sample preparation questionable.

Method A: Saturated 2.0 ml H₂O overnight, 0.5 ml of filtrate diluted to 10.0 ml with methanol, added 1 drop of 6 N KOH to UV cell.

Method B: Saturated 5.0 ml H₂O overnight, 1.0 ml of filtrate diluted with 0.01 N HCl (10 to 250 fold dilutions).

TABLE III

Method Comparison - 2,4-Diamino-5-methyl-6-[(3,4,5-trimethoxyanilino)methyl]quinazoline Salts

| | Acid Conc. (M) | Acid pH | Acid/Base | Solubility mg base/ml | Filtrate pH |
|---|---|---|---|---|---|
| Isethionic | .1 | 1.20 | 2/1 | 16.33* | 1.83 |
| | .05 | 1.46 | 1/1 | 17.34* | 3.70 |
| | Prepared Salt | | | 24.8 | 5.30 |
| Ethoxyacetic | .1 | 2.20 | 2/1 | 19.5* | |
| | .065 | 2.35 | 1/1 | 19.7* | 4.15 |
| | Prepared Salt | | | 6.3 | 5.32 |
| Methane | .1 | 1.00 | 1/.9 | 8.74 | |
| | .06 | 1.42 | 1/1 | 6.5 | 3.00 |
| | Prepared Salt | | | 4.9 | 5.32 |
| Benzene sulfonic | .1 | 0.95 | 2/1 | 7.17 | 2.95 |
| | .05 | 1.48 | 1/1 | 1.89 | 2.95 |
| | Prepared Salt | | | 1.24 | 4.45 |
| Glycolic | .1 | 2.68 | 2/1 | 4.13 | 3.00 |
| | .1 | 2.69 | 1/1 | 4.73 | 3.28 |
| | Prepared Salt | | | 2.55 | 5.30 |

*Not saturated, base solubility equals amount of base available in shake out preparation.

The compounds of this invention may be administered orally, parenterally or rectally.

In accordance with the invention, oral pharmaceutical compositions are produced by formulating the compounds of the invention, as the active ingredient, in dosage unit forms with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into a teaspoon or other standard container. Some examples of suitable pharmaceutical carriers, including pharmaceutical diluents, are gelatin capsules; sugars such as lactose and sucrose; starches such as corn starch and potatoe starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The compounds of the invention when intended for parenteral use could be dissolved in an isotonic aqueous solution containing other materials such as buffers, preservatives, etc. It may also be placed in the form of an sterile lyophilized material to be taken up in an appropriate vehicle at time of use.

Lastly, the compounds of the invention may be administered in the form of a suppository using glycerin, cocoa butter, etc., as a vehicle. The vehicle may also contain preservatives and coloring agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 100 mg, preferably 2 to 50 mg of the active ingredient per dosage unit so that the entire amount to be administered during a day can be made up from a reasonable number of dosage units.

The compounds can be combined with other antimalarial compounds, such as quinine, chloroquine, etc., and used in the above described manner.

The compounds of the invention inhibit the growth of pathogenic bacteria, such as *Streptococcus faecalis* (MGH-2), normal (UC-76) and drug-resistant (S18713) *Staphyloccus aureus; Escherichia coli* (Vogel) and *Shigella sonnei* (C-10). Thus, the compounds would be useful in the sterilization of laboratory glassware, etc.

STARTING MATERIALS

2-Hydroxyethanesulfonic acid solution

A solution of 10 g of 2-hydroxyethane sulfonic acid, sodium salt in 30 ml of H₂O is eluted through 120 g of an acid form ion exchange column [Dowex 50WX8 (Dow Chemical Co., Midland, Mich.)]. The resulting acidic solution (200 ml) is titrated and found to be 0.304 molar in the desired acid.

EXAMPLE 1

2,4-Diamino-5-methyl-6-[(3,4,5-trimethoxyanilino)methyl]quinazoline monoisethionate A slurry of 2,4-diamino-5-methyl-6-[(3,4,5-trimethoxyanilino)methyl]quinazoline monoacetate (59.2 g) Great Britain Patent Specification No. 1,345,502 in water (1.5.1) at 80° C. is treated with acetic acid (200 ml). The resulting solution is made basic (pH 10) by addition of 50% NaOH. The slurry is cooled by addition of ice and the solid collected. Drying (100° C., 1 torr, 2 hours) gives the free base as a light green-yellow powder.

A slurry of the free base (22.9 g) in acetone (1 l) is treated with 0.304 M aqueous 2-hydroxyethanesulfonic acid (204 ml) cooled and filtered to remove a small amount of solid. The filtrate is concentrated to a solid which is recrystallized from a mixture of ethanol (400 ml) and acetone (400 ml) and dried (80° C., 1 torr, 4 hours) to give the title compound, mp 189°–191° C.

EXAMPLE 2

2,4-Diamino-5-methyl-6-[(3,4,5-trimethoxyanilino)methyl]quinazoline D-glucuronate A mixture of 2,4-diamino-5-methyl-6-[(3,4,5-trimethoxyanilino)methyl]quinazoline (1.0 g) and glucuronic acid (0.7 g) in methanol (65 ml) is heated to dissolve the solid. The solution is cooled to 10° C. and filtered to remove a small amount of solid. The filtrate is heated to reflux and ethyl acetate is added to the cloud point. The warm solution is filtered then slowly cooled. The solid that forms is collected, washed first with ethylacetate, then with ether and dried in vacuo at 60° C. to give the salt as a yellow powder with no definite melting point.

I claim:

1. A compound of the formula

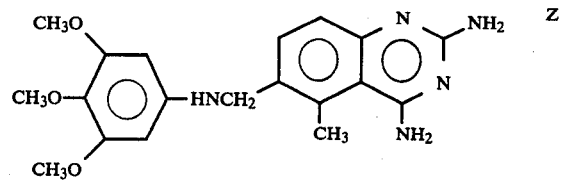

wherein Z is 2-hydroxyethanesulfonic acid or glucuronic acid.

2. The compound of claim 1 having the name 2,4-diamino-5-methyl-6-[(3,4,5-trimethoxyanilino)methyl]-quinazoline monoisethionate.

3. The compound of claim 1 having the name 2,4-diamino-5-methyl-6-[(3,4,5-trimethoxyanilino)methyl]-quinazoline glucuronate.

4. The compound of claim 2 being in crystalline form.

5. The compound of claim 3 being in powdery form.

* * * * *

UNITED STATES PATENT AND TRADEMARK OFFICE

CERTIFICATE EXTENDING PATENT TERM
UNDER 35 U.S.C. § 156

PATENT NO.      :   4,376,858

ISSUED          :   March 15, 1983

INVENTOR(S)     :   Norman L. Colbry

PATENT OWNER    :   Warner Lambert Company

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,286 days from the original expiration date of the patent, October 31, 2000, with all rights pertaining thereto as provided by 35 U.S.C. § 156(b).

I have caused the seal of the Patent and Trademark Office to be affixed this 6th day of January 1997.

Bruce A. Lehman
Assistant Secretary of Commerce and
  Commissioner of Patents and Trademarks